(12) United States Patent
Hessler

(10) Patent No.: US 6,751,288 B1
(45) Date of Patent: Jun. 15, 2004

(54) SMALL ANGLE X-RAY SCATTERING DETECTOR

(75) Inventor: Jan P. Hessler, Downers Grove, IL (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 2 days.

(21) Appl. No.: 10/261,657

(22) Filed: Oct. 2, 2002

(51) Int. Cl.⁷ .............................................. G01N 23/201
(52) U.S. Cl. ........................................ 378/86; 378/87
(58) Field of Search ............................. 378/70, 86–90, 378/207; 250/366–368; 385/116

(56) References Cited

U.S. PATENT DOCUMENTS 6,163,592 A * 12/2000 He et al. ...................... 378/71
6,330,301 B1 * 12/2001 Jiang ............................ 378/85

* cited by examiner

Primary Examiner—Edward J. Glick
Assistant Examiner—Therese Barber
(74) Attorney, Agent, or Firm—Brian J. Lally; Daniel D. Park; Paul A. Gottlieb

(57) ABSTRACT

A detector for time-resolved small-angle x-ray scattering includes a nearly constant diameter, evacuated linear tube having an end plate detector with a first fluorescent screen and concentric rings of first fiber optic bundles for low angle scattering detection and an annular detector having a second fluorescent screen and second fiber optic bundles concentrically disposed about the tube for higher angle scattering detection. With the scattering source, i.e., the specimen under investigation, located outside of the evacuated tube on the tube's longitudinal axis, scattered x-rays are detected by the fiber optic bundles, to each of which is coupled a respective photodetector, to provide a measurement resolution, i.e., dq/q, where q is the momentum transferred from an incident x-ray to an x-ray scattering specimen, of 2% over two (2) orders of magnitude in reciprocal space, i.e., $q_{max}/q_{min} \cong 100$.

7 Claims, 2 Drawing Sheets

SMALL ANGLE X-RAY SCATTERING DETECTOR

CONTRACTUAL ORIGIN OF THE INVENTION

The United States Government has rights in this invention pursuant to Contract No. DE-AC02-98CH10913 between the U.S. Department of Energy (DOE) and The University of Chicago representing Argonne National Laboratory.

FIELD OF THE INVENTION

This invention relates generally to x-ray scattering detectors wherein incident x-rays are scattered by the electrons of a sample specimen under investigation and is particularly directed to apparatus for time-resolved measurement of small-angle scattered x-ray intensity by complex molecules such as proteins.

BACKGROUND OF THE INVENTION

Small-angle X-ray scattering (SAXS) detectors are increasingly being used for the analysis of the composition and characteristics of materials in solid, liquid or vapor form. For example, SAXS is used in protein science for characterizing the conformational states of proteins and the kinetics of protein refolding by using an intense x-ray beam focused on a protein sample in solution. The electrons of the sample under investigation scatter a portion of the flux of the incident x-ray beam and the scattered x-ray beam intensity is measured as a function of the scattering angle. From the x-ray scattering data, the protein's overall size (radius of gyration), overall shape (pair distribution function) and association state may be determined. This type of SAXS analysis is currently the only known time-resolved approach capable of determining these values.

In the field of SAXS material analysis, however, there is a problem with optimization of the time/rate of data acquisition. More specifically, current SAXS detectors are typically modified x-ray crystallography detectors which are not optimized for SAXS data acquisition. There is thus a need to improve the performance and capabilities of SAXS material analysis by providing a fast detector capable of accurate time resolution specifically designed for use in SAXS applications.

The present invention addresses the aforementioned limitations of the prior art by providing apparatus for directing an x-ray beam onto a specimen under investigation and then detecting the x-rays scattered by the specimen after transiting an evacuated tube. A flat, disc-shaped detector provided with a fluorescent screen and concentric rings of first fiber optic bundles is disposed on the distal end of the tube for detecting x-rays scattered over small angles, and an annular detector also incorporating a fluorescent screen and second fiber optic bundles is concentrically disposed about an intermediate portion of the tube for detecting x-rays scattered over larger angles.

OBJECTS AND SUMMARY OF THE INVENTION

Accordingly, it is an object of the present invention to provide an arrangement for detecting x-rays scattered at small angles from a material being analyzed having high resolution and a wide dynamic range of measurement of momentum transfer of the incident x-rays.

It is another object of the present invention to provide for the more efficient detection of x-rays scattered over small angles by a material being analyzed such as a large, complex protein molecule on a time-resolved basis.

A further object of the present invention is to provide a fast detector for the time resolution measurement of the intensity of x-rays scattered over small angles by a complex molecule such as naphthalene in a gas phase sample.

This invention contemplates apparatus for detecting small-angle scattering of x-rays by a specimen being analyzed, the apparatus comprising an evacuated, cylindrical tube having a longitudinal axis and first and second opposed ends disposed on the axis, wherein x-rays are directed along the axis and onto the specimen disposed adjacent the tube's first end; a first detector disposed on the second end of the tube for detecting x-rays scattered by the specimen over a first angular range relative to the longitudinal axis of the tube; and a second detector disposed concentrically about and intermediate the first and second ends of the tube for detecting x-rays scattered by the specimen over a second angular range, wherein the second angular range is greater than the first angular range.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

DETAILED DESCRIPTION OF THE PREFERRED EMBODIMENT

Figure 1:
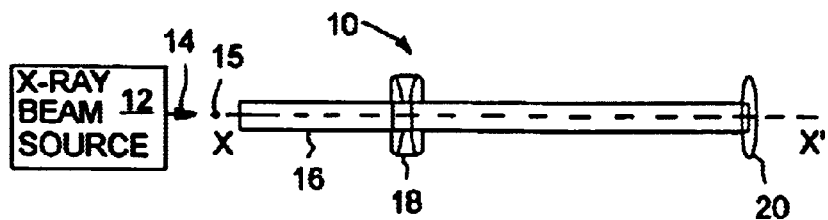
FIG. 1 is a simplified combined schematic and block diagram of a small-angle x-ray scattering detector in accordance with the principles of the present invention.

Referring to FIG. 1, there is shown a simplified combined block and schematic diagram of a small-angle x-ray scattering detector 10 in accordance with the present invention. Detector 10 is comprised of an evacuated, elongated, linear tube 16 disposed adjacent a scattering source, or target, 15. The scattering source 15 is the specimen undergoing analysis and may be in the form of a solid, a liquid, or a gas. An x-ray beam source 12 is disposed adjacent the scattering source 15 for directing an x-ray beam 14 thereon. The incident x-rays interact with the electrons of the scattering source 15, with the scattered x-ray intensity measured as a function of the scattering angle of the scattered x-rays relative to a longitudinal axis X—X of tube 16. From the scattering data, various parameters of the scattering source 15 can be determined, such as, for example, in the case of a protein molecule, its molecular size (radius of gyration), overall molecular shape (pair distribution function), and association state can be inferred. It should be noted that FIG. 1 is not drawn to scale. For example, in one embodiment of the invention, the evacuated tube 16 is 1.5 meters long and is spaced 2 meters from the scattering source 15. Forming a vacuum within tube 16 eliminates atmospheric scattering of x-rays and results in more accurate, complete specimen analysis data.

The evacuated tube 16 includes a first end disposed adjacent the scattering source 15 and a second, opposed end. Disposed on the second end of the evacuated tube 16 is an end plate detector 20 for detecting x-rays scattered over small angles. The end plate detector 20 is disc-like in shape and is shown in plan view in FIG. 3. The end plate detector 20 includes a first fluorescent screen 24 (shown in dotted line form) and the terminal ends of plural fiber optic bundles that are arranged in concentric, circular arrays for detecting scattered x-rays. Thus, the end plate detector 20 includes first, second, third and fourth fiber optic bundle rings 40, 42, 44 and 46. Each of the fiber optic bundle rings includes plural spaced terminal ends of fiber optic bundles. Thus, the first fiber optic bundle ring 40 includes the terminal ends of plural fiber optic bundles 40a, while the second fiber optic bundle ring 42 includes plural spaced terminal ends of second fiber optic bundles 42a. Similarly, the third fiber optic bundle ring 44 includes plural spaced terminal ends of third fiber optic bundles 44a, while the fourth fiber optic bundle ring 46 includes plural spaced terminal ends of fourth fiber optic bundles 46a. Fluorescent screen 24 is disposed over the terminal ends of the fiber optic bundles for emitting photons in response to x-rays incident upon the fluorescent screen. Each of the individual fiber optic bundles is coupled to a respective detector, such as a photodiode. Thus, the fiber optic bundles in the first ring 40 are connected to photodiodes 48, while the fiber optic bundles in the second ring 42 are connected to photodiodes 50. Similarly, the fiber optic bundles in the third ring 44 are connected to photodiodes 52, while fiber optic bundles in the fourth ring 46 are connected to photodiodes 54. A metallic structure (not shown for simplicity) is connected to and supports the fluorescent screen 24 and fiber optic bundles and maintains these elements in fixed position.

Figure 3:
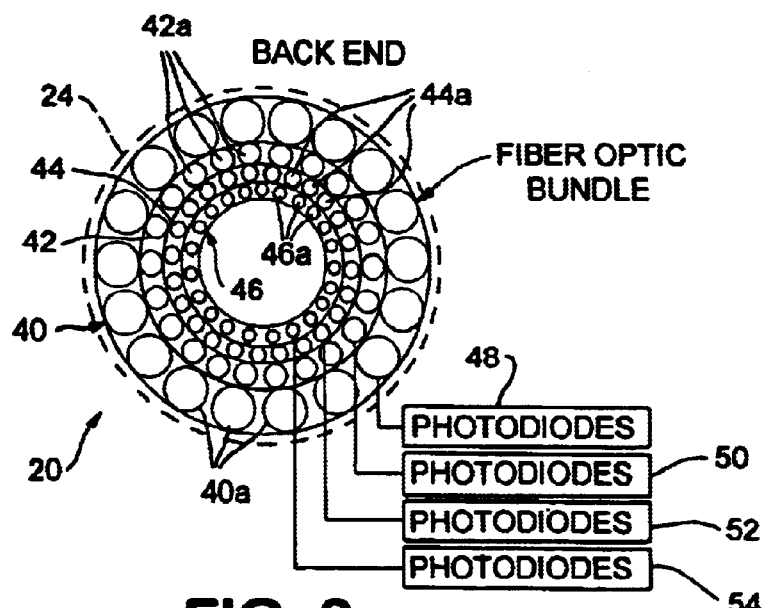
FIG. 3 is a simplified plan view of an end plate detector for use on an end of the linear tube of the small-angle x-ray scattering detector of FIG. 1 which includes a fluorescent screen and concentric rings of fiber optic bundles for detection of scattered x-rays in accordance with another aspect of the present invention.

As can be seen from FIG. 3, all of the fiber optic bundles within a given ring have substantially the same cross sectional area. It can also be seen that the cross sectional area of the individual fiber optic bundles increases in proceeding away from the longitudinal axis of the evacuated tube at the center of the concentric ring configuration. Thus, the fiber optic bundles 40a in the first ring 40 have a larger cross sectional area than the fiber optic bundles 42a in the second ring 42, which, in turn, has fiber optic bundles with a greater cross sectional area than those of the third ring 44. Finally, the third ring 44 includes fiber optic bundles 44a which are larger in cross sectional area than the fiber optic bundles 46a in the fourth ring 46.

Figure 2:
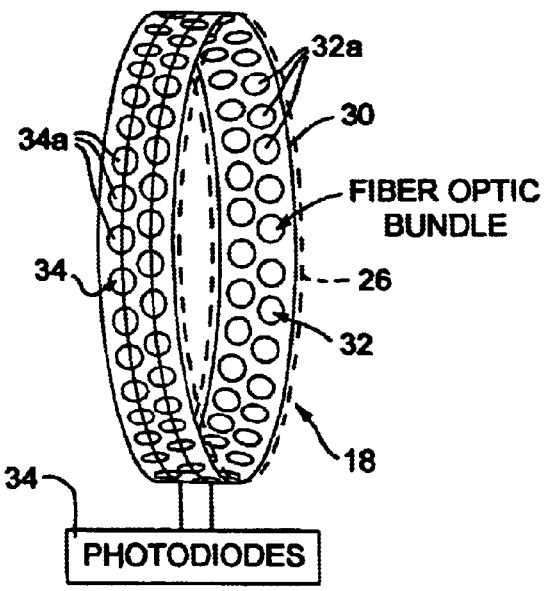
FIG. 2 is a simplified perspective view of an annular detector comprised of fluorescent screens and plural fiber optic bundles concentrically disposed about the linear tube shown in the apparatus of FIG. 1 in accordance with one aspect of the present invention.

Referring to FIG. 2, there is shown a simplified perspective view of an annular detector 18 disposed about the tube 16 as shown in FIG. 1 for detecting x-rays scattered at larger angles from axis X—X' and those detected by end plate detector 20. Annular detector 18 includes a support ring 30 connected to first and second fiber optic bundle rings 32 and 36. A second fluorescent screen 26 (shown in dotted line form) is disposed over the ends of the fiber optic bundles for converting incident x-rays to photons which, in turn, are incident on the fiber optic bundles. Each of the fluorescent screens is on the order of 0.1 mm thick. The first and second fiber optic bundle rings respectively include plural spaced fiber optic bundles 32a and 36a which are maintained in fixed position concentrically disposed about tube 16 by support ring 30. The first and second fiber optic bundle rings 32, 36 are arranged in a spaced manner along the length of the tube 16 parallel to its longitudinal axis X—X'. The fiber optic bundles within the first and second fiber optic bundle rings 32, 36 are coupled to photodiodes 34, with each fiber optic bundle coupled to a respective photodiode for providing an electronic signal in response to receipt of a scattered x-ray by the fiber optic bundle. Annular detector 18 is disposed along the length of the tube 16 so that the fiber optic bundles within the annular detector detect x-rays scattered at angles larger than those detected by the end plate detector 20. By properly positioning annular detector 18 along the tube 16 and selecting its radius, x-rays scattered at angles greater than those detectable by end plate detector 20 will be detected so as to provide continuous x-ray detection from 0° deflection angle to a selected maximum deflection angle.

The standard expression for the transferred momentum of the incident x-rays is given by $$q = 4\pi/\lambda \sin \theta. \tag{1}$$

Differentiation gives $$dq/d\theta = 4\pi/\lambda \cos \theta. \tag{2}$$

Now we can write $$dq/q = \cos\theta/\sin\theta \, d\theta = \cos\theta \, dS/\sin\theta R \tag{3}$$

where
 dS=arc length
 dθ=subtended angle
 R=radius of circle
Alternately, we can write $$d\theta = \sin\theta/\cos\theta \, dq/q. \tag{4}$$

Solving for R, we have $$R = \cos\theta \sin\theta \, dS/f \tag{5}$$

where f=dq/q is the desired precision in the measurement of the transferred momentum, i.e., the ratio of the change in momentum to the momentum that can be detected. Note, the above expression is independent of x-ray wavelength, R→∞ as θ→0, and R→0 as θ→π/2.

To design a practical detector we must specify dS and the maximum length of the detector, $D_{max}$. From these two parameters we can define the minimum angle that will give this result. That is $$\theta_{min} = \arctan dS/fD_{max}. \tag{6}$$

For example, for dS=1 mm, $D_{max}$=1000 mm, and f=0.04, we have $\theta_{min}$=arctan(1/40) or $\theta_{min}$=2.4995×10$^{-2}$. Similarly, if we let $D_{max}$=2000 mm, we may decrease f by a factor of two, keeping the same dS and have the same $\theta_{min}$. The radius of the detector at this maximum distance from the source is $D_{max}$=sin $\theta_{min}$. X-rays scattered closer to the axis can still be detected, but if we wish to achieve a constant dq/q, we must then change dS in this region. Since this region is relatively small, this is, indeed, possible.

First, we select the parameters, dS, $D_{max}$, and f=dq/q. With this information, we use equation (6) above and calculate $\theta_{min}$. To calculate the other positions, we set $\theta_1 = \theta_{min}$, $R_1 = D_{max} \sin \theta_{min}$, and calculate $\theta_2$ from $$\theta_2 = \theta_1 + \sin\theta_1/\cos\theta_1 \, dq/q = f \sin\theta_1/\cos\theta_1. \tag{7}$$

With $\theta_2$ we can then calculate $R_2$ from $$R_2 = dS/f \cos\theta_2/\sin\theta_2. \quad (8)$$

We generalize the above two equations and obtain $$\theta_j = \theta_{j-1} + f \sin\theta_{j-1}/\cos\theta_{j-1} \quad (9)$$

and $$R_j = dS/f \cos\theta_1/\sin\theta_1. \quad (10)$$

Figure 4:
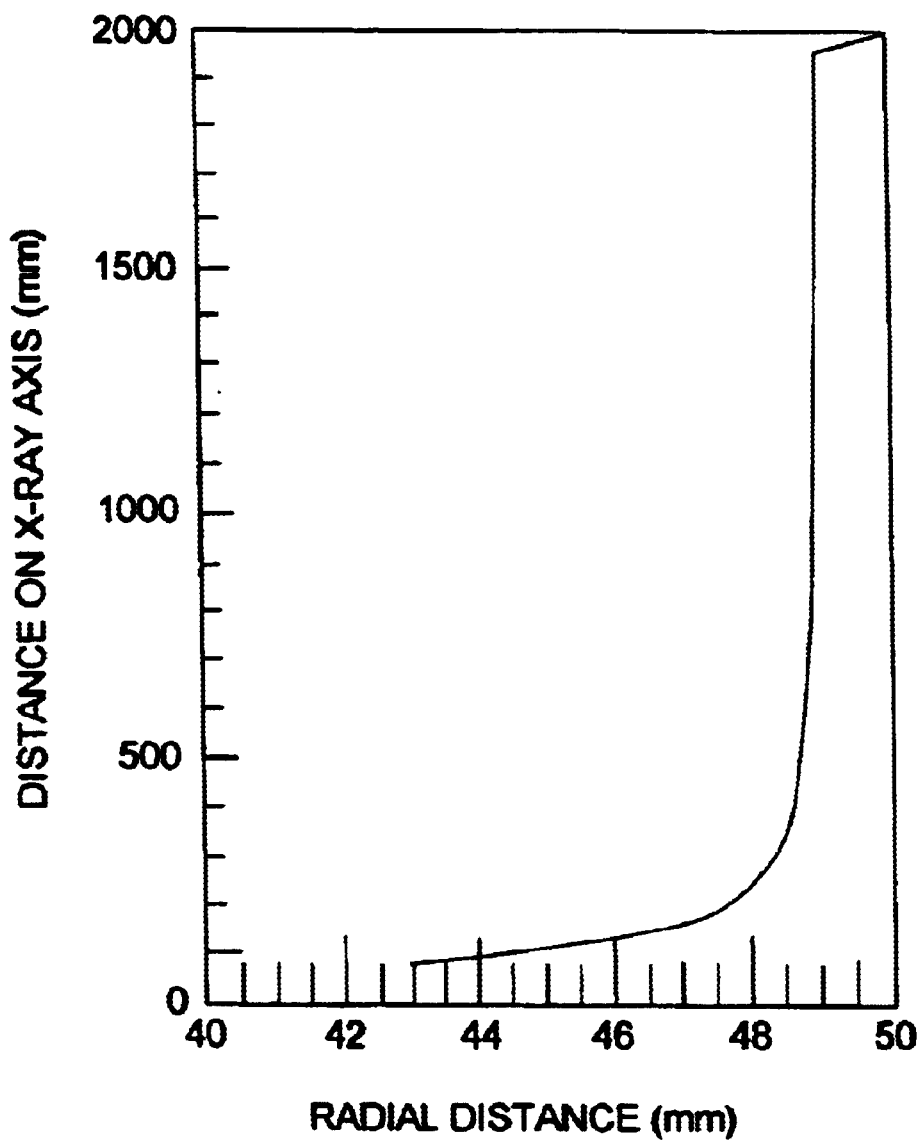
FIG. 4 is a graphic representation of the radial distance of detection from the detector's axis along the length of the axis of the detector in the present invention.

A plot of the positions is shown in FIG. 4 where we have chosen dS=1 mm, $D_{max}$=2000 mm, and f=dq/q=0.02. From this plot, we find that not only does the sampling point come closer to the axis of the x-rays as the scattering angle increases, but it almost remains at nearly the same distance from the x-ray beam for most of the length of the system. This may mean that we can design a system for a precision of 2%, etc., build an end piece with a diameter of about 50 mm (2 inches) and then add on as many additional values of the transferred momentum as we can afford. From FIG. 4, it appears that detectors may be added along the axis from 2000 to 500 mm without really changing the diameter of the detector. This results in a reduction in the cost of building this invention. Note, at the 500 mm position there are only seventy (70) detectors mounted along the axis. With these detectors, the present invention is capable of scanning two orders of magnitude in reciprocal space, i.e., $q_{max}/q_{min} \cong 100$. The current GOLD detector used at Argonne National Laboratory has $q_{max}/q_{min} \approx 75/2 = 37.5$. Therefore, in addition to higher temporal resolution, the present invention will also significantly increase the range in reciprocal space that may be measured in a single experiment.

Now consider the inner part of the detector that is located at $D_{max}$. The outer radius of the end part of the detector is given by $$R_1 = D_{max} \sin\theta_{min}. \quad (11)$$

We may rewrite equation (3) above as $$dS = D_{max} dq/q \sin\theta/\cos\theta. \quad (12)$$

Now we use the small angle approximation, $\cos\theta = 1$ and $\sin\theta \cong S/D_{max}$, and write $$dS = dq/qS = fS. \quad (13)$$

Therefore, we have a sequence of rings where the radius of each inner ring is smaller than its neighbor by 1-f. We therefore write $$S_2 = (1-f)S_1 = (1-f)D_{max} \sin\theta_{min}. \quad (14)$$

This equation may be generalized to give $$S_n = (1-f)^{n-1} D_{max} \sin\theta_{min}. \quad (15)$$

If we now set the smallest ring equal to the radius of the beam-stop, $R_{stop}$, we have $$R_{stop} = (1-f)^{n-1} D_{max} \sin\theta_{min}. \quad (16)$$

Solving this equation for n, we obtain $$n = 1 + \ln(R_{stop}/D_{max} \sin\theta_{min})/\ln(1-f). \quad (17)$$

Putting numbers in, we have $$n = 1 + \ln(2/50)/\ln 0.98 \cong 160 \quad (18)$$

The radial extent of the innermost ring is given by $dS_n = fR_{stop} = 40 \,\mu m$. This is feasible. We may want to put a single silicon detector in the center with rings out to a radius on the order of 10 mm, then follow this with fiber optic bundles out to the end of the flat detector. Note, this total detector will have something like 160+70=230 rings. This is not unreasonable. Analog-to-digital filters are available for this type of optical detector arrangement.

While particular embodiments of the present invention have been shown and described, it will be obvious to those skilled in the relevant arts that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

The embodiment of the invention in which an exclusive property or privilege is claimed is defined as follows:

1. Apparatus for detecting small-angle scattering of x-rays by a specimen being analyzed, said apparatus comprising:
   an evacuated, cylindrical tube having a longitudinal axis and first and second opposed ends disposed on said axis, wherein x-rays are directed along said axis and onto the specimen disposed adjacent the tube's first end;
   a first detector disposed on the second end of said tube for detecting x-rays scattered by the specimen over a first angular range relative to the longitudinal axis of said tube, the first detector being disc-shaped; and
   a second detector disposed concentrically about and intermediate the first and second ends of said tube for detecting x-rays scattered by the specimen over a second angular range, wherein said second angular range is greater than said first angular range.

2. The apparatus of claim 1 wherein said first and second detectors respectively include respective fluorescent screens and first and second plural fiber optic bundles concentrically disposed about the longitudinal axis of said tube.

3. The apparatus of claim 2 further comprising plural photodetectors each coupled to a respective fiber optic bundle.

4. The apparatus of claim 2 wherein said first plural fiber optic bundles are arranged in plural annular arrays, with each annular array of said first fiber optic bundles disposed in a radially spaced manner from the longitudinal axis of said tube and from other annular arrays of first fiber optic bundles.

5. The apparatus of claim 4 wherein each of said first fiber optic bundles has a generally circular cross section with the fiber optic bundles in a given annular array all having the same cross sectional area, and wherein the cross sectional areas of the fiber optic bundles in said annular arrays increases in proceeding away from the tube's longitudinal axis, wherein said tube has a radius $r_1$ and said first detector has a radius $r_2$, where $r_2 > r_1$.

6. The apparatus of claim 2 wherein said second plural fiber optic bundles are arranged in plural rings disposed in a spaced manner along the length of and centered on the longitudinal axis of said tube, each of the said plural rings being equally spaced from the longitudinal axis of said tube.

7. Apparatus for analyzing the composition and characteristics of a specimen material, said apparatus comprising:
   a source of x-rays directed onto the specimen material, wherein said x-rays are scattered by the specimen material in accordance with the composition and characteristics of the specimen material;
   an evacuated tube-like chamber having first and second opposed end portions, wherein said first end portion is disposed in facing relation to said source of x-rays and the specimen material is disposed intermediate said source of x-rays and the first end portion of said evacuated chamber;

a first detector disposed on the second end portion of said chamber and responsive to x-rays incident thereon for detecting x-rays scattered over a first set of angles relative to an axis defined by said source of x-rays and said chamber; and a second detector concentrically disposed about a portion of said tube-like chamber intermediate its first and second opposed ends and responsive to x-rays incident thereon for detecting x-rays scattered over a second set of angles relative to said axis, wherein the angles of said second set are greater than the angles of said first set.

* * * * *